US00PP08968P

United States Patent [19]

Henry

[11] Patent Number: Plant 8,968

[45] Date of Patent: Nov. 8, 1994

[54] FLORIBUNDA ROSE PLANT NAMED 'KATELYN ANN'

[75] Inventor: Pat. T. Henry, Rte. 3, Box 1930, Laurens, S.C. 29360

[73] Assignee: Pat. T. Henry, Laurens, S.C.

[21] Appl. No.: 986,445

[22] Filed: Oct. 6, 1993

[51] Int. Cl.[5] ..... A01H 5/00

[52] U.S. Cl. ..... Plt./26

[58] Field of Search ..... Plt. 1, 26, 22

*Primary Examiner*—Howard J. Locker

[57] ABSTRACT

A new cultivar of rose plant of the Floribunda class distinctive in character by its fully double, medium pink flowers; abundant and continual blooming; and the unusual blend of coloring, shape, and fragrance of the flower.

1 Drawing Sheet

BACKGROUND OF THE INVENTION

The present invention relates to a new and distinct variety of floribunda rose, a seedling resulting from a definite effort to produce an improvement in this class of roses.

SUMMARY OF THE INVENTION

Primary features of this variety with connote a distinction over existing varieties are the vigorous, abundant, and continual blooming taken with the perfection of the fully double flowers of an old-fashioned type more particularly apparent in the accompanying illustration of a specimen thereof.

BRIEF DESCRIPTION OF THE DRAWING

The accompanying illustration depicts stems, foliage, flower buds, and flowers in various stages of development, depicted in color as nearly true as it is reasonably possible to make the same in a color illustration of this character, said illustration having been taken in an outdoor garden environment in Laurens, S.C., USA in May, 1992. Photographic coloration and actual plant description may vary slightly due to lighting, flower aging, weather conditions, and time of day and month. The color terminology set forth in accordance with the Reinhold Color Atlas depicts true and characteristic coloration of the plant under normal sunlight conditions.

DETAILED BOTANICAL DESCRIPTION

The following is a detailed description of the new variety, color terminology being in accordance with the "Reinhold Color Atlas" by A. Kornerup and J. H. Wanscher, and published by Reinhold Publishing Corporation (1961).

Variety denomination: Katelyn Ann.

Type: Hardy, Bush, Outdoor, seedling, for cut flowers and garden decoration.

Class: Floribunda.

Propagation: Holds its distinguishing characteristics through succeeding asexual propagation by cuttings.

The rose plant was grown at Laurens, S.C., USA, and was derived as follows:

Female (seed) parent: Unknown (seeds collected from unlabeled rose hips).

Male (pollen) parent: Unknown.

The operation of the artificial pollination is therefore expressed by the following: (unknown×unknown).

The following observations were made of specimens grown outdoors in Laurens, S.C., USA, during May 1992.

PLANT DESCRIPTION

Plant:

*Height.*—90–106 cm.

*Habit.*—Upright, with vigorous branching.

Branches:

*Length.*—Stem length averages 25 cm.

*Color.*—Young stems are Grayish Green 28D7; tinged with red. Adult wood is Deep Green 28E8.

*Thorns.*—Average in size and quantity. Color is Grayish green.

Leaves: Upper surface glossy. Foliage is dense.

*Stipules.*—Medium Green and broad. Finely dentate at edges, some glandular hairs. 2 wings.

*Petioles.*—Upper side is flat with raised edge and a few glandular hairs. Under side is medium green with occasional small thorns.

*Leaflets.*—3 to 5 leaflets per compound leaf, 5 occurring most often; leaflets 3 cm. in length on average; leaf margin is serrated.

*Color.*—Young foliage (upper surface), Dark green 27F8, tinged with red, (under surface), Deep green 28E8. Adult foliage (upper surface), Dark green 27F6, (under surface), Dark green 27E5.

INFLORESCENCE

Numbers of flowers: From 1 to 5, but generally 3.

Peduncle: Thick, light green, rigid, ligh red glandular aciculas (needlelike bristles), with occasional small prickles. Average length is about 5 cm.

Sepals: Upper side is Deep green 28D8 and under side is Grayish green 28C4, and are covered in moderately fine hair. Sepals have glabrous edges with occasional wings which are covered in fine hair. Sepals do not extend beyond the apex of the bud.

Bud:

*Shape.*—Ovoid.

*Length.*—2 cm. on average.

*Size.*—Small.

Flower:

*Shape.*—Medium and flat shaped with small compacted petals in center (old garden look).

*Diameter.*—7 cm. on average.

*Color.*—(When opening) Upper side is Greenish yellow 1A8 at base, merging into Dull red 8B3, and Under side is Yellow 2A6 at base, merging into Dull red 10B4. (When blooming) Upper side is Light yellow 1A5 at base, merging into Reddish gray 8B2, and Under side is pastel yellow 2A4 at base, merging into Pale red 11A3 at very outside edge. (When finished blooming) Upper side is Pale yellow 3A3 merging into Reddish gray 10B2, and Under side is Yellow 2A6 turning to Rose pink 12A5.

*Fragrance.*—Very strong and fruity, held throughout all stages of bloom.

*Lastingness.*—Very good. Averages 10 days on the plant and 7 days as a cut flower.

Petals:

*Shape.*—Ovate with a truncated base.

*Texture.*—Silky to the touch, strong, resilient to withstand strain without tearing, tough.

*Number.*—60 on average. Petals arranged in overlapping circles.

*Petaloids.*—About 15 on average, very small, tightly compacted in center of bloom, old garden look.

*Cleaning.*—Good.

REPRODUCTIVE ORGANS

Stamens:

*Number.*—30 on average, pollen not present.

*Anthers.*—Light yellow 3A5.

*Filaments.*—Yellow 3A7 and of variable length.

Pistils:

*Number.*—30 on average.

*Stigmas.*—Yellow 3A7.

*Styles.*—Greenish yellow 1a6 and very hairy.

*Receptacle.*—Yellow 3A7 and in the form of a shallow cup. Hips and seeds have not been observed.

The development:

*Vegetation.*—Vigorous.

*Blooming.*—Abundant and continual throughout the season (May through October).

Resistance to fall frost is good. Foliage will withstand light frost or freeze (32 degree F. for average 2 hours) without foliage damage.

Resistance to diseases is very good. No blackspot or powdery mildew noticed in Laurens, S.C., with a 14 day interval fungicide spray program.

I claim:

1. A new and distinct floribunda rose plant substantially as herein described and illustrated.

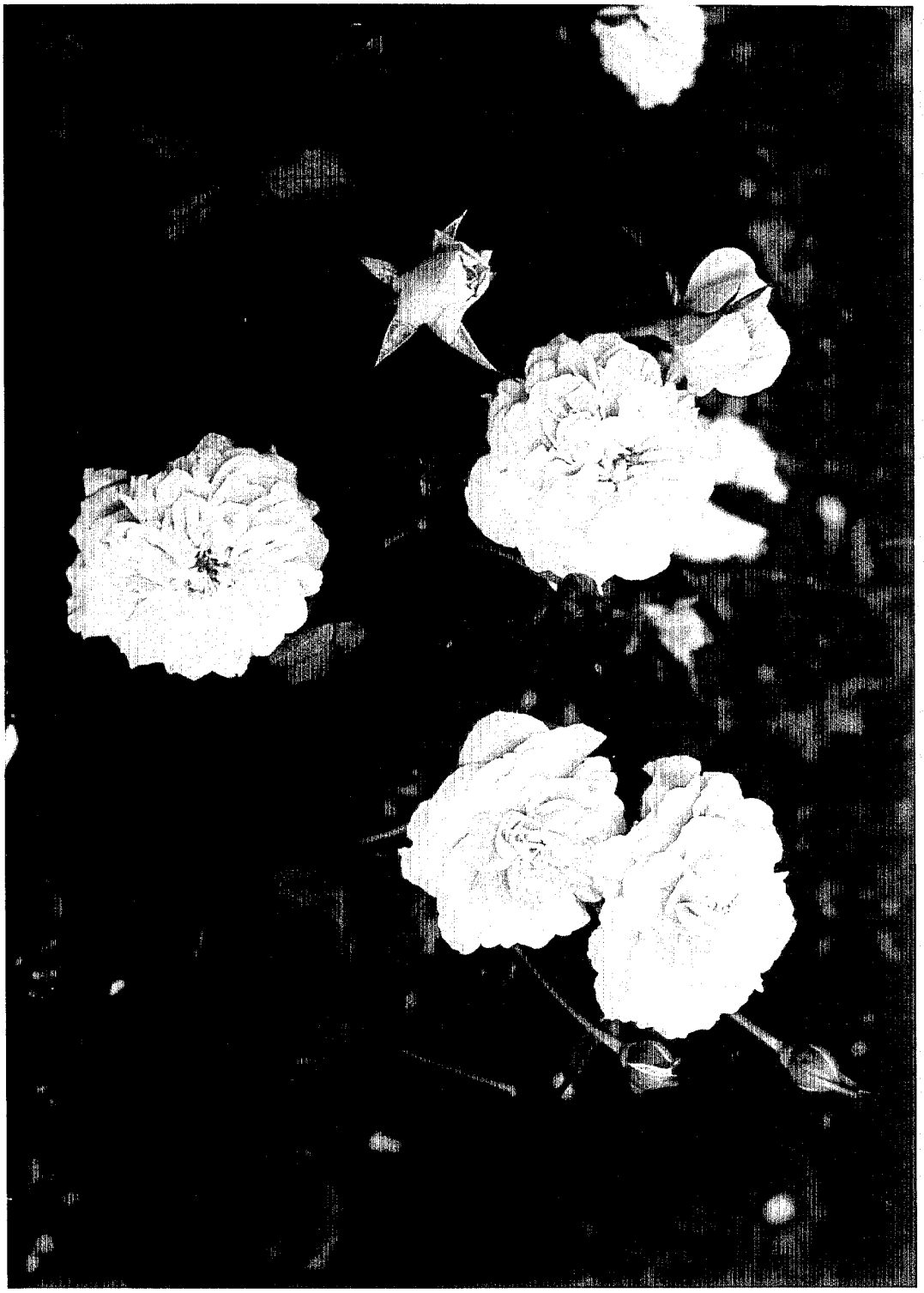

* * * * *